United States Patent [19]
Buehler et al.

[11] Patent Number: 5,364,589
[45] Date of Patent: Nov. 15, 1994

[54] METHOD AND APPARATUS FOR STERILIZING BIOLOGICAL WASTE

[75] Inventors: James A. Buehler, Ft. Myers; Lynnford W. Claypoole, Naples, both of Fla.

[73] Assignee: Sterile Systems, Inc., Sanibel, Fla.

[21] Appl. No.: 677,999

[22] Filed: Apr. 1, 1991

[51] Int. Cl.⁵ ............................................. A61L 2/16
[52] U.S. Cl. ...................................... 422/26; 422/27; 422/32; 422/297; 422/300; 422/309
[58] Field of Search .................. 422/26, 32, 300, 309, 422/27, 297; 241/DIG. 38

[56] References Cited

U.S. PATENT DOCUMENTS

| | | | |
|---|---|---|---|
| 3,180,740 | 4/1965 | Martin | 422/27 |
| 3,721,527 | 3/1973 | Lodige et al. | 422/26 |
| 3,839,843 | 10/1974 | Stewart, Jr. | 422/27 |
| 4,284,600 | 8/1981 | Gillis et al. | 422/26 |
| 4,374,491 | 2/1983 | Stortroen et al. | 422/26 |
| 5,048,766 | 9/1991 | Gaylor et al. | 241/DIG. 38 |
| 5,091,158 | 2/1992 | Drauschke et al. | 422/26 |

FOREIGN PATENT DOCUMENTS 0277507  8/1988  European Pat. Off. ............ 422/300

Primary Examiner—Timothy M. McMahon
Attorney, Agent, or Firm—William E. Noonan

[57] ABSTRACT

A method and apparatus are disclosed for sterilizing biological waste. The waste material is introduced into a shredder mechanism to chop the material into particles of reduced size, which are transmitted into a preheating chamber. Steam is introduced into the chamber to preheat the particles to at least 140 degrees Fahrenheit. A selected amount of the preheated particles are continuously transmitted into a sterilization chamber and steam is introduced into the sterilization chamber to heat the preheated particles to at least 248 degrees Fahrenheit for a sufficient duration such that the particles are sterilized.

17 Claims, 4 Drawing Sheets

METHOD AND APPARATUS FOR STERILIZING BIOLOGICAL WASTE

FIELD OF THE INVENTION

This invention relates to a method and apparatus for sterilizing biological waste and, in particular, to a system for sterilizing contaminated medical products and byproducts.

BACKGROUND OF THE INVENTION

Large amounts of hazardous medical waste are generated by hospitals, clinics, veterinarians, undertakers, physical therapists and other sources. Sterilizing and disposing of such "red bag" waste material, as well as other forms of contaminated biological waste products, has become an increasingly expensive and annoying concern.

Several generally accepted methods of treating medical waste are presently available. These include incineration, chemical treatment and steam sterilization. However, each such technique exhibits certain shortcomings.

Incinerators are usually unsightly and expensive. Moreover, they tend to pollute the environment. Medical waste is a particular problem for incinerators because such waste typically comprises about 30%-35% plastic. When such material is burned, a variety of hazardous gases are emitted. As a result, incinerators are often subjected to burdensome governmental regulations relating to emissions, safety, zoning, and permitting. Emissions may be severely restricted, for example, to five hundred pounds of waste burned per hour. Alternatively, for handling larger amounts of waste, expensive, scrubbing may be required. All medical waste incinerators must employ afterburners, which greatly increase fuel usage. In short, the expense, inefficiency and regulation of incinerators makes their use impractical in most situations.

Sterilizing chemicals present their own set of problems. Ethylene oxide is dangerously explosive and poisonous. Formaldehyde is flammable and toxic. Chemicals also can be difficult to test and transport. And, like incinerators they are typically subjected to close monitoring and extensive government regulation.

Steam sterilization has been employed to sanitize medical equipment and red bag waste. However, conventional steam systems are usually quite inefficient for waste. Typically, such systems include a room size chamber that must be heated to a predetermined sterilizing temperature of approximately 250 degrees Fahrenheit for a predetermined time (e.g. 30 minutes). Such chambers may exhibit cool spots and experience expensive time delays during the heating up and cooling down stages. Moreover, a variety of viruses, bacteria and, in particular, bacterial spores can often survive the steam treatment because of cold spots and other problems. And, in order to prevent the cold spots due to air being present, an elaborate pumping system is required to draw air out of the chamber and replace that air with steam. Additionally, conventional steam systems are not cost efficient for treating a single bag or container of waste. Typically, the system is not operated until a large batch of waste is available. As a result, large amounts of contaminated material can be stored untreated, often for a substantial period of time.

SUMMARY OF THE INVENTION

It is therefore an object of this invention to provide an improved method and apparatus for sterilizing biological waste, wherein an increased number of bacteria, viruses, spores and other living contaminants in the waste are efficiently and effectively destroyed.

It is a further object of this invention to provide an apparatus for sterilizing biological waste that permits even relatively small amounts of waste to be continuously introduced and sterilized without shutting down the apparatus and without exposing the operator to contamination.

It is a further object of this invention to provide an improved method and apparatus for sterilizing biological waste that is safer, cleaner, less expensive and more energy efficient than conventional techniques.

It is a further object of this invention to provide a method and apparatus for sterilizing biological waste, which does not produce toxic byproducts and reduces pollutants to a low level.

It is a further object of this invention to provide a method and apparatus for sterilizing biological waste, which requires significantly less governmental regulation that is required by conventional techniques.

It is a further object of this invention to provide a method and apparatus for sterilizing biological waste, which is particularly effective for contaminated medical waste.

This invention results from a realization that improved sterilization of biological waste may be accomplished by preheating the waste with steam prior to the final steam Sterilization process. This invention results from the further realization that even small amounts of biological waste may be sterilized effectively and efficiently by first chopping or shredding the waste to improve heat transfer, then preheating the chopped waste particles and finally introducing those particles in a gradual, controlled manner into a steam sterilization chamber, where the sterilization process is completed.

This invention features a method of sterilizing biological waste material. The waste material is introduced into a shredder mechanism to chop the material into particles of reduced size. Those particles are then transmitted into a preheating chamber and steam is introduced into the chamber to preheat the particles to at least 140 degrees Fahrenheit. A selected amount of the preheated particles are continuously transmitted to a sterilization chamber and steam is introduced into the sterilization chamber to heat the preheated particles to at least 248 degrees Fahrenheit. This heating is conducted for a sufficient duration such that the particles are sterilized.

In a preferred embodiment the particles are preheated to at least 140 degrees Fahrenheit, but no greater than 210 degrees Fahrenheit. The preheated particles are preferably heated in the sterilization chamber to no greater than 330 degrees Fahrenheit. The preheated particles may be heated to 248 degrees F. for a duration of from 30 minutes to 40 minutes, to 330 degrees Fahrenheit for a duration of 10 minutes to 15 minutes, and to intermediate temperatures for respective durations between 10 minutes and 40 minutes.

The method may further include selectively transmitting the heated particles to a compactor and compacting those particles therein. The chopped particles may be conveyed through and dispersed in the preheating chamber as the steam is introduced thereto. The preheated particles may be conveyed through and dispersed in the sterilization chamber as steam is introduced thereto.

This invention also features an apparatus for sterilizing biological waste material. The apparatus includes a shredder mechanism and means for introducing the waste into the shredder mechanism to chop the waste into particles of reduced size. There are means defining a preheating chamber and first transmittal means for selectively transmitting the particles from the shredder mechanism to the preheating chamber. There are means for introducing steam into the preheating chamber to preheat the particles to at least 140 degrees Fahrenheit. There are also means defining a sterilization chamber. Second transmittal means are employed for continuously transmitting a selected amount of the preheated particles from the preheating chamber to the sterilization chamber. Means are provided for introducing steam into the sterilization chamber to heat the preheated particles to at least 248 degrees Fahrenheit for a sufficient duration such that the particles are sterilized.

Preferably, a particle compactor is employed and third transmittal means are used for transmitting the sterilized particles to the compactor, wherein the particles are compacted. The means for introducing may include a feed hopper connected to the shredder mechanism. The apparatus may also include purge means that comprise means for introducing steam into the feed hopper to kill bacteria therein after the waste material has been introduced to the shredder mechanism.

The first transmittal means may include a storage chamber disposed between the shredder mechanism and the preheating chamber. A first valve may selectively transmit the chopped particles from the shredder mechanism to the storage chamber and a second valve may selectively transmit the chopped particles from the storage chamber to the preheating chamber. The second transmittal means may include a valve assembly for continuously transmitting a selected amount of preheated particles from the preheating chamber to the sterilization chamber. The third transmittal means may include a valve apparatus for selectively transmitting the sterilized particles from the sterilization chamber to the compactor.

A jacket is preferably formed about the preheating chamber and means may be provided for introducing steam into the jacket to heat the exterior surface of the preheating chamber. Similarly, a jacket may be formed about the sterilization chamber and means may be provided for introducing steam into that jacket to heat the exterior surface of the sterilization chamber.

A preheating conveyer may be employed to convey the particles through the preheating chamber from the first transmittal means to the second transmittal means. The preheating conveyer may include means for dispersing the particles as the particles are conveyed through the preheating chamber. A sterilization conveyer may be utilized for conveying the preheated particles through the sterilization chamber from the second transmittal means to the third transmittal means. The sterilization conveyer may include means for dispersing the particles as the particles are conveyed through the sterilization chamber.

DISCLOSURE OF PREFERRED EMBODIMENT

Other objects, features and advantages will occur from the following description of a preferred embodiment and the accompanying drawings, in which.

Figure 1:
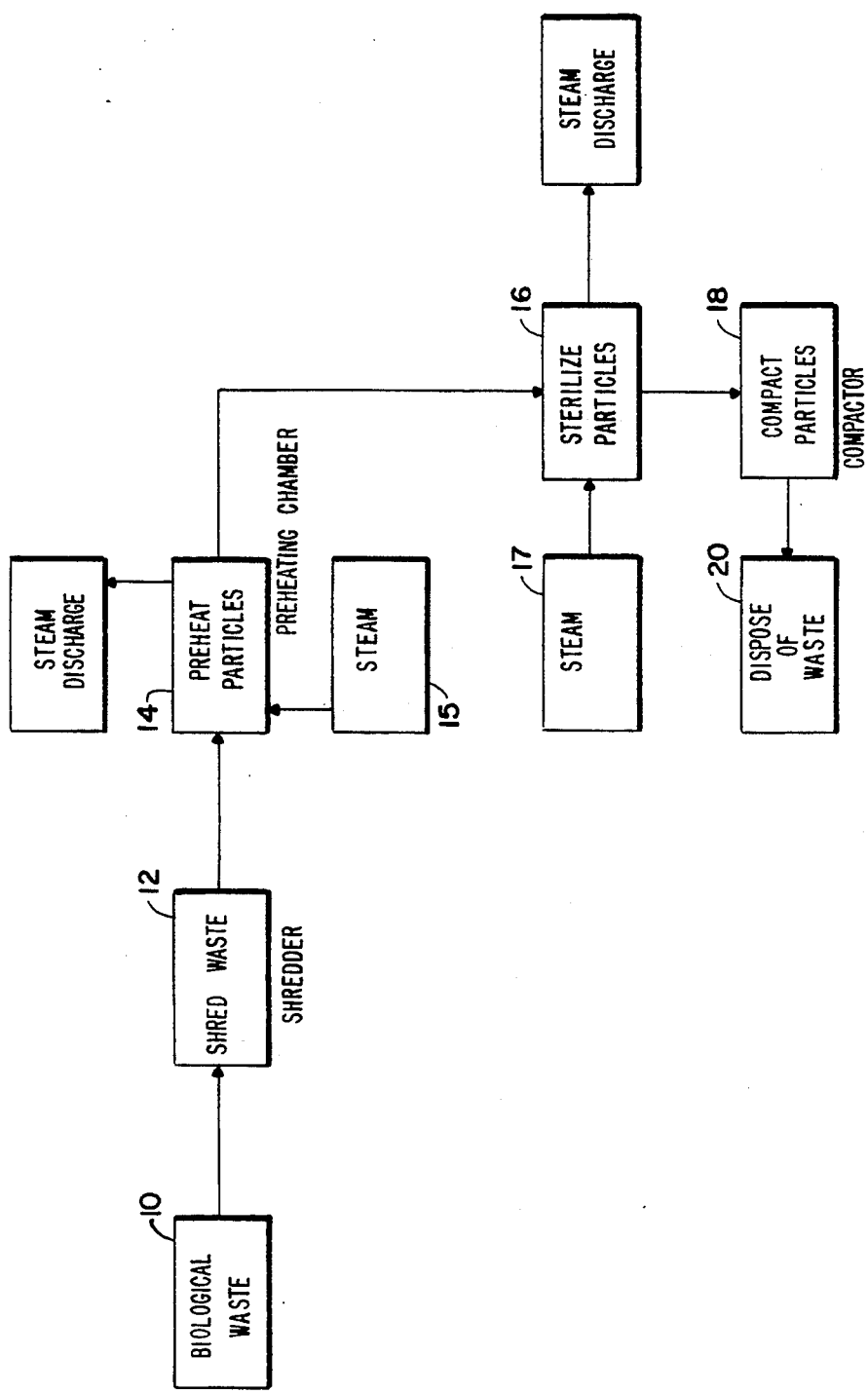
FIG. 1 is a diagram of a method for sterilizing biological waste according to this invention.

There is shown in FIG. 1 a method of sterilizing and disposing of biological waste 10. Such waste may comprise bandages, gauze, disposable gloves and garments, syringes and needles, materials of glass and other medical byproducts commonly designated as "red bag waste". Other types of biological waste may also be successfully processed. Initially, the waste is introduced into a shredder or chopper mechanism 12, where it is chopped into fine particles, preferably having a size which is smaller than 2" in any dimension. The chopped particles are then delivered to a preheating chamber 14. Therein, the particles are preheated to a temperature of at least 140 degrees Fahrenheit, and preferably approximately 165 degrees Fahrenheit, by steam 15 that is introduced into the chamber. During this step the particles are preheated and it is believed that pasteurization occurs, whereby a substantial portion of the vegetative cells are killed. The particular duration of preheating step is arbitrary and not a limitation of this invention. The particular time duration and temperature are selected to achieve an optimally efficient operation. For example, at a preheating temperature of 165 degrees the particles are preferably heated for a duration of approximately 15 minutes. It is believed that in this time approximately 90% of the vegetative bacterial cells are destroyed. Although the temperature and time duration of the preheating step may be varied somewhat within the limitations of this invention, there are typically practical constraints. Although increasing the time and temperature increases the percentage of bacteria that are destroyed, it may also necessitate a more expensive and inefficient operation. Accordingly, it is preferred that, during the preheating stage, the temperature be kept below 210 degrees Fahrenheit and the preheating be performed for no longer than 20 minutes. At times and temperatures above these levels, the additional bacteria that are destroyed typically do not justify the increased energy requirements.

The efficiency of this preheating step is improved considerably because the particles are shredded or chopped prior to the preheating step. This increases the surface area of the waste and permits heat to be transferred much more effectively through the biological waste as it is preheated, so that vegetative bacterial extermination is enhanced.

Although it is believed that a large majority of the vegetative bacteria are destroyed during the preheating stage, additional living viral contaminants, and bacterial spores, remain in the waste. Accordingly, the preheated particles are delivered to a sterilization chamber 16 wherein they are heated by steam 17 to a temperature of at least 248 degrees Fahrenheit (120 degrees Centigrade). Again, the particles enhance the heat transfer and significantly improve the sterilization process. The particles are heated in chamber 16 for a period of 30 minutes, although the precise duration is not a limitation of this invention. Nonetheless, the steam sterilization of the particles continues for a sufficient time such that the remaining biological contaminants are killed and the particles are thereby sterilized. If the sterilization process is conducted at a temperature higher than 248 degrees Fahrenheit, a time commensurately less than 30 minutes may be required. For example, if a temperature of 266 degrees Fahrenheit (130 degrees Centigrade) is employed, a duration of 15 minutes is typically sufficient to exterminate most of the spores and remaining bacteria. The longest practical duration for the sterilization process is approximately 40 minutes and the highest practical temperature at which the sterilization process may be operated is 330 degrees Fahrenheit. Within these time and temperature limits, the precise temperature and time duration of the sterilization process are selected to achieve a desired level of bacterial extermination. This level can be tested through the use of conventional bacterial test strips.

Upon completion of the sterilization process, the sterilized particles are delivered to a compactor 18 wherein they are compacted in a conventional manner. The compacted particles are then disposed of, step 20, in an appropriate conventional manner.

Figure 2:
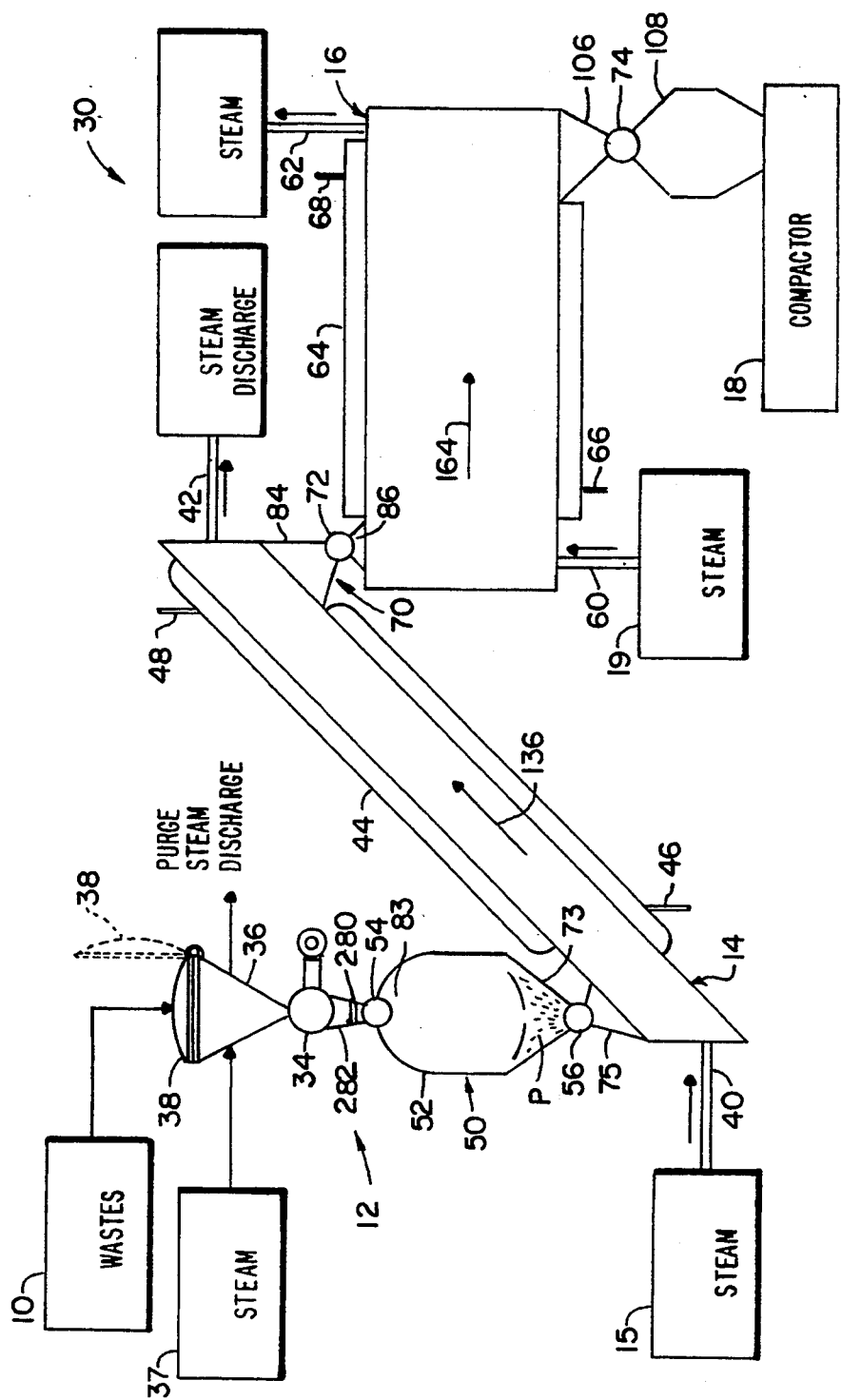
FIG. 2 is an elevational, partly schematic view of an apparatus for sterilizing biological waste according to this invention.

An apparatus 30 for accomplishing the method of this invention is shown in FIG. 2. Shredder mechanism 12 includes a conventional shredder or chopper device 34 and a feed hopper 36 for introducing material 10 into shredder 34. A lid 38 is pivotably secured to hopper 36 for selectively covering and uncovering the entrance thereof. A source of purge steam 37 is connected to hopper 36. This steam serves to decontaminate the hopper following the chopping operation, as described more fully below.

Preheating chamber 14 includes an elongate, generally cylindrical enclosure. An inlet 40 interconnects chamber 14 with the source of preheating steam 15. An outlet 42 at opposite end of chamber 14 discharges preheating steam from the interior of the chamber. As a result, free-flowing steam may be provided through chamber 14. Chamber 14 houses a conventional screw conveyer. A jacket 44 is wrapped about the exterior surface of chamber 14. Jacket 44 includes an inlet 46 and an outlet 48 for conducting steam and condensate respectively into and out of the jacket. This jacket operates to maintain the temperature in the preheating chamber in the manner described more fully below.

First transmittal means 50 are provided between the shredder mechanism 12 and the preheating chamber 14. More particularly, the first transmittal means include a storage chamber 52 and a first valve 54, shown alone in FIG. 3, for selectively transmitting material from the shredder device 34 to the storage chamber 52. In particular, first valve 54 comprises a conventional star valve having preferably four identical compartments 51, 53, 55 and 57. In an alternative embodiment the valve 54, and any of the other valves described below may include an alternative number of compartments. The valve is operated in a known manner under the direction of a microprocessor (described below) or otherwise such that it rotates in the direction of arrow 59. Each of the compartments 51–57 is communicably aligned once during each rotation with a discharge portion 282 of shredder 34 and an inlet portion 83 of storage chamber 52.

Figure 4:
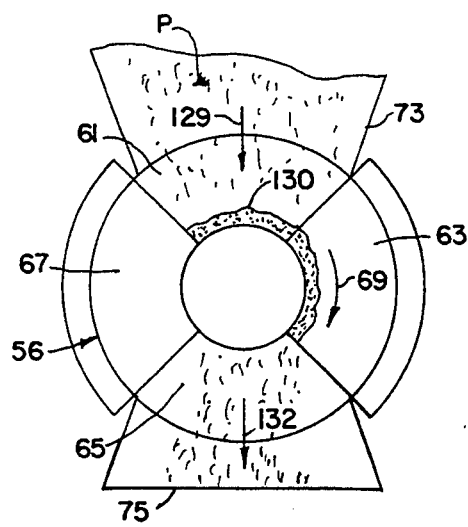
FIG. 4 is a schematic view of a second star valve for transmitting chopped particles from the storage chamber to the preheating chamber in a controlled manner.

A second valve 56, shown alone in FIG. 4, is located at the opposite lower end of storage chamber 52 for selectively transmitting material from the storage chamber to the preheating chamber 14. Second valve 56 comprises a four compartment star valve having compartments 61, 63, 65 and 67. Valve 56 is likewise controlled by a microprocessor or other control means to rotate in the direction of arrow 69.

Sterilization chamber 16, FIG. 2, has an inlet 60 that interconnects the chamber with a source of sterilizing steam 19. An outlet 62 discharges the sterilizing steam from chamber 16, such that free-flowing steam may be provided through chamber 16. The sterilizing chamber may comprise various types of conventional mechanisms for moving waste material through and dispersing that material in the sterilization chamber. For example, the sterilization chamber may include a conventional paddle-type conveyer or a conventional helical or screw-type conveyer. Alternatively, various other types of conveyers may be utilized. A jacket 64 is disposed about the outer surface of sterilization chamber 16. Jacket 64 includes an inlet 66 and an outlet 68 for respectively introducing steam into and removing steam from the jacket. The jacket is preferably maintained at a pressure of about 20–25 psig such that the exterior surface of the sterilizing chamber is held at a desired temperature. Each of the compartments 61–67 communicably aligns once each rotation with discharge chute 73 of storage chamber 52 and inlet 75 of preheating chamber 14.

Figure 5:
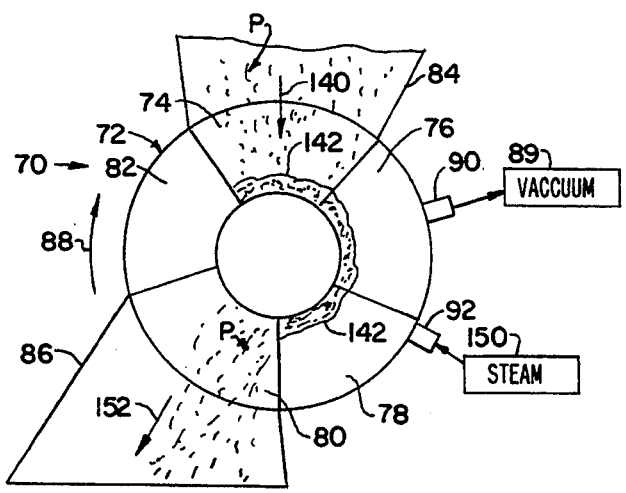
FIG. 5 is a schematic view of a third star valve for continuously transmitting preheated waste particles from the preheating chamber to the sterilizing chamber.

Sterilization chamber 16 is selectively connected to preheating chamber 14 by second transmittal means 70, shown alone in FIG. 5. The second transmittal means 70 includes a star valve assembly 72 having five identical compartments 74, 76, 78, 80 and 82. The second transmittal means 70 also includes a discharge chute 84 depending from preheating chamber 14 and an inlet section 86 formed in sterilization chamber 16. Valve 72 is rotatable in the direction of arrows 88 by a controller or otherwise. During each rotation, each of the compartments 74–82 is communicably aligned with the discharge chute 84 and the inlet section 86. Additionally, a vacuum port 90 and a steam injection port 92 are engaged with valve 72 such that during each rotation of the valve each of the compartments communicates with each of the ports 90 and 92.

Figure 6:
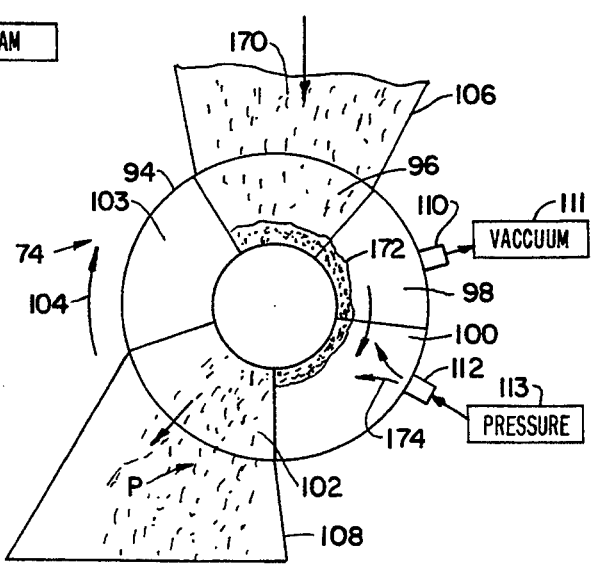
FIG. 6 is a schematic view of a fourth star valve for transmitting sterilized waste particles from the sterilizing chamber to the compactor.

At the completion of the sterilization stage, the waste material is transmitted from chamber 16 to compactor 18 through a third transmittal means 74, shown alone in FIG. 6. Third transmittal means 74 includes a fourth star valve 94, which has five identical compartments 96, 98, 100, 102 and 103. Valve 94 is driven, again typically by a controller, in the direction of arrow 104. The third transmittal means also includes a discharge chute 106 depending from sterilization chamber 16 and an inlet section 108 formed into compactor 18. During each rotation of valve 94, each of the compartments 96–103 is communicably aligned with the chute 106 and the discharge section 108. Also during each rotation, each of the compartments is communicably aligned with a vacuum outlet 110 and a pressurizing port 112.

Figure 3:
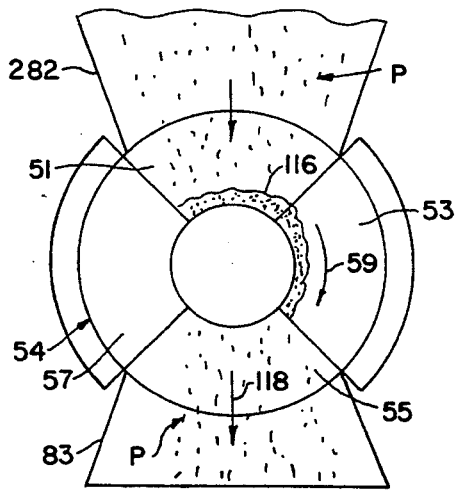
FIG. 3 is a schematic view of a first star valve for transmitting chopped waste particles from the shredder mechanism to the storage chamber.

With reference to FIGS. 2–6, apparatus 30 operates to sterilize biological waste in the following manner. Hopper cover 38 is opened to the position shown in phantom and red bag waste 10 is introduced into the feed hopper 36. The hopper channels the waste into shredder device 34, which shreds or chops the waste material into particles of reduced size. A screen 280 having openings of a predetermined size is disposed in or below the shredder so that only fine particles of waste are discharged from shredder device 34. More particularly, screen 280 blocks passage of particles that are more than 2″. Preferably the screen openings are ¼″ by ¼″, so that particles larger than ¼″ are not discharged. As shown in FIGS. 2 and 3, chopped particles P fall through discharge chute 282 of shredder device 34 and into the compartments 51, 53, 55 and 57 of rotating star valve 54. As a result, the particles collect as a pile 116 in each successive compartment. Valve 54 continues to rotate in the direction of arrow 59 and, as each compartment aligns with section 83, the particles P are discharged from the compartment in the direction of arrow 118 into section 83 of storage chamber 52. This process continues until the waste 10 is completely shredded or chopped. At that point, the shredder is shut off and valve 54 is stopped. As a result, the valve is closed and the chopped particles are not allowed to re-enter the shredder device 34; rather they remain securely within the storage chamber 52.

After feed hopper 36 is emptied, the hopper is purged of residual contaminants by steam purge 37, which is injected through the feed hopper with the lid 38 closed and locked. This steam is introduced at approximately 212 degrees Fahrenheit and 0 psig for a selected time. At the completion of the purge cycle, the lid 38 is reopened and new material waste may be introduced.

When valve 56 is in an "off" condition, it does not operate and therefore seals the bottom of storage chamber 52 so that particulate waste material P collects in the chamber. The waste is not transmitted into preheating chamber 14 unless and until the chamber is sufficiently heated. This is accomplished by introducing steam 15, FIG. 2, at a pressure of approximately 15 psig into chamber 14 through inlet 40. The steam is discharged through outlet 42 and is free-flowing. The internal temperature of the preheating chamber is raised in this manner to at least 140 degrees Fahrenheit, and preferably at least 165 degrees Fahrenheit, and the pressure is maintained slightly above zero psig so that free flowing steam is provided through the preheating chamber. When these conditions are sensed, valve 56 is operated in the manner shown in FIG. 4. Chopped particles P fall in the direction of arrow 129 through chute 73 of storage chamber 52 and into the revolving compartments 61, 63, 65 and 67. A pile of waste 130 collects in each compartment and as each compartment aligns with inlet 75, the particles P are deposited in the direction of arrow 132 through the inlet 75 and into preheating chamber 14. The valve continues to rotate until the emptied compartment returns to communicable alignment with discharge chute 73 in order to receive additional particles from the storage chamber.

The conveyer housed by preheating chamber 14 is operated to drive the chopped particles through the chamber in the direction of arrow 136, FIG. 2 such that the particles are heated by the steam. More particularly, the screw conveyer moves the particles helically through the chamber. During each turn of the conveyer the particles are tumbled and dispersed so that heat transfer is increased. The particles are driven to the upper end of chamber 14 and upon reaching that end they may be returned to the opposite lower end of the conveyer by a suitable baffling apparatus. The particles are heated by the free-flowing steam to at least 140 degrees Fahrenheit and preferably 165 degrees Fahrenheit. This continues for a selected time (e.g. 20 minutes) during which a significant portion of the vegetative bacteria and other living microscopic contaminants are destroyed. At the same time, steam is introduced into jacket 44 through inlet 46 and is maintained therein at a pressure of approximately 20 psig. This helps to reduce heat loss from chamber 14 so that the particles are adequately preheated.

During the preheating period, star valve 72, FIGS. 2 and 5, remains in an "off" condition so that access from chamber 14 to sterilizing chamber 16 is blocked and all of the chopped particles remain in chamber 14 for the desired preheating duration. At the completion of the preheating stage, valve 72 is driven in the direction of arrows 82. Each successive compartment 74, 76, 78, 80 and 82 communicably engages discharge chute 84 to receive particles P, as well as steam and air from the preheating chamber 14. This material falls, in the direction of arrow 140, into the aligned compartment and the particles form a pile 142 therein.

The compartment then rotates into communicable engagement with vacuum port 90. As exhibited by compartment 76, vacuum 90 draws a vacuum in the engaged compartment thereby removing the air and steam from the compartment. This step is performed to maintain the desired temperature in chamber 16. If the air from the preheating chamber is introduced into the sterilizing chamber, where the pressure is 15 psig, that air will have a temperature of only 224.6 degrees Fahrenheit, which is significantly below the required sterilization temperature of 248 degrees Fahrenheit. Such relatively cool air would tend to disrupt the sterilization process and would create significant inefficiencies in the system. Because the air is removed, however, such temperature fluctuations and inefficiencies are avoided.

As valve 72 continues to rotate, each compartment is next engaged with pressurizing port 92. Steam 150 at 15 psig is introduced through port 92 into the compartment so that the compartment is pressurized. As a result, when the compartment then rotates into alignment with sterilizing chamber inlet 86, the particles P and attendant steam are deposited in the direction of arrows 152 through inlet 86 into sterilization chamber 16. Without the addition of steam 150, the vacuum drawn in the compartment would tend to hold the pile 142 of particles P in the compartment as it engages the inlet 86.

After the particles P are deposited into the sterilization chamber, the valve 72 continues to rotate in the direction of 88 so that the compartment previously aligned with inlet 86 is in the position of compartment 82. Finally, the compartment is rotated to the position of compartment 74, in substantial alignment with discharge chute 84 from preheating chamber 14, so that additional preheated particles may be collected.

The preheated particles are conveyed through and dispersed in chamber 16 by an appropriate conveyer. As previously described, this may comprise a paddle-type or screw-type conveyer. As the particles are conveyed and dispersed, free-flowing sterilizing steam 19 is introduced into chamber 16 through inlet 60 and discharged therefrom through inlet 62. This steam heats the particles in the chamber to at least 248 degrees Fahrenheit and maintains the pressure inside the chamber at 15 psig. Once again, steam is introduced through jacket 64 to heat the exterior of the sterilization chamber and maintain the sterilizing temperature within the chamber. The particles are driven in the direction of arrow 164 through the chamber. Again, a suitable baffle may be constructed by those skilled in the art, such that when the particles reach the right hand of the sterilization chamber their direction is reversed. The particles continue to be driven through the conveyer and heated to at least 248 degrees Fahrenheit for a desired duration. As stated above, when the minimum temperature is employed, this duration should be for at least 30 minutes. The sterilizing period may be reduced if higher temperatures are utilized.

During the sterilizing stage, valve 74, FIGS. 2 and 6, remains in an "off" condition so that access between sterilization chamber 16 and compactor 18 is blocked. When the sterilization step is completed, valve 74 is started and driven rotatably in the direction of arrow 104. As a result, compartments 96, 98, 100, 102 and 103 are successively aligned with discharge chute 106 from chamber 16. This allows sterilized particles and accompanying steam 170 to enter the aligned compartment, e.g. compartment 96.

The valve 94 continues to rotate until the compartment reaches the position of compartment 98. At this point the compartment is engaged with vacuum port 110 and a vacuum is drawn on the compartment. As a result, the remaining steam is removed from the compartment and a pile of sterilized particles 172 remains.

The compartment then rotates to the position of compartment 100, and air 113 is introduced into the compartment through port 112 in the direction of arrows 174 such that the compartment is pressurized. As a result, when the valve continues to rotate and the compartment reaches the position of compartment 102, particles P fall through the inlet 108 into compactor 18, FIG. 2. The sterilized particles are compacted therein and are removed and disposed of in a conventional manner.

The effectiveness of the preheating and sterilizing steps may be tested by employing a known spore sample containing a predetermined amount of bacterial spores of a known heat resistant species. This sample is introduced, such as through an entrance in the storage chamber and is allowed to run through the preheating and sterilizing chambers. At the completion of these stages the sample is investigated and the percentage of bacteria destroyed is determined. If increased sterilization is required, the times and temperatures of the respective stages may be adjusted accordingly.

Figure 7:
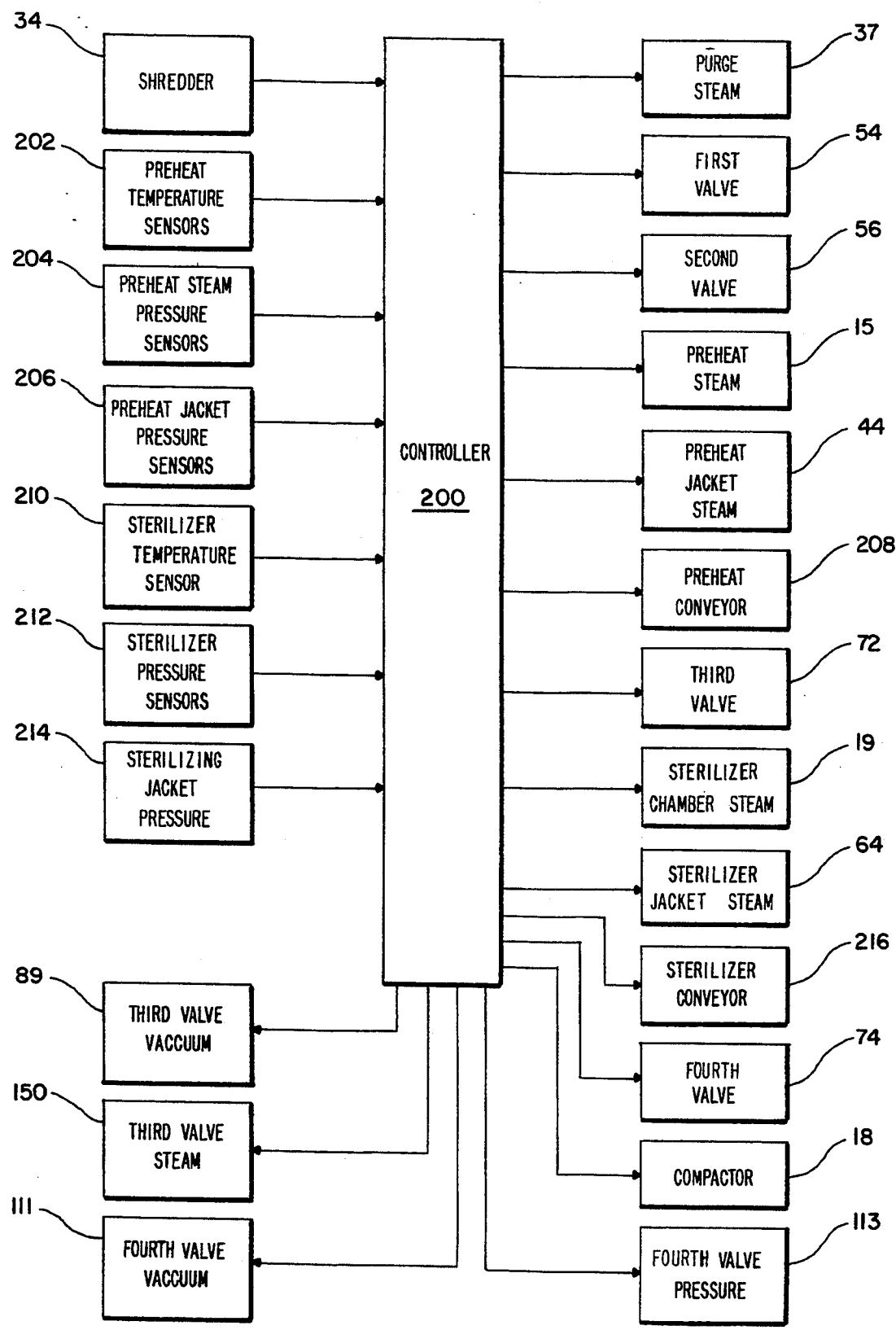
FIG. 7 is a diagram of a controller for automatically operating the apparatus of FIG. 2.

The apparatus 30 shown in FIG. 2 may be either manually or automatically controlled. As shown in FIG. 7, a controller 200 may be utilized to automatically control operation of the system. Controller 200 may comprise a conventional microprocessor or alternative means known to those skilled in the art. The controller receives inputs from shredder 34. When the shredder is "on" the controller maintains first valve 54 in an open condition so that chopped particles fall into the storage chamber. When shredder 34 is turned off the controller responds by closing valve 54 and initiating the introduction of purge steam 37 into the feed hopper. The controller receives preheat temperature and pressure inputs and a jacket pressure input from sensors 202, 204, and 206, respectively. When the required conditions are met in the preheat chamber, second valve 56 is operated, as described above, to transmit chopped particles into chamber 14 for preheating. At the same time, the controller directs steam 15 into the preheating chamber so that the required parameters are maintained. If the steam pressure in preheat jacket 44 is insufficient the controller 200 directs additional steam into the jacket. If cool spots develop in the preheat chamber, such cool spots are typically detected by sensor 202 and as a result, controller 200 stops valve 56 so that the transmission of chopped particles into the preheated is blocked until the required temperature level is regained. Controller 200 likewise provides an output to control the preheat conveyer 208. If the temperature inside preheat chamber 14 is insufficient, the conveyer is stopped until a sufficient temperature is reached. The controller is also programmed with the required time duration for the preheating stage. At the completion of this period, preheat steam 15 and preheat conveyer 208 are stopped and valve 56 is closed.

A second group of temperature and pressure sensors 210, 212 and 214 are provided for the sterilization chamber. Each provides an input to controller 200. At or about the completion of the preheating stage, the controller initiates introduction of sterilizing steam 19 into chamber 16 and commences operation of sterilizer conveyer 216. The controller also commences operation of third star valve 72 so that preheated particles are transmitted to the sterilization chamber. The sterilizing process is then continued for a preprogrammed duration. Again, if the temperature or pressure parameters for sterilization chamber 16 fall below their required levels, the controller 200 may either halt the operation of valve 72 and conveyer 216 or increase the level of either the sterilizing steam 19 or the jacket steam 64. During the sterilizing stage, the controller also provides outputs to control the vacuum 89 drawn on valve 72 and the steam 150 subsequently introduced into the valve.

At the completion of the preprogrammed sterilizing time, valve 72 is stopped to block access between the preheating chamber and the sterilization chamber. Fourth star valve 74 is now operated so that sterilized particles are transmitted from the sterilization chamber to compactor 18. The controller instructs the compactor to perform its operation. During the transmission of the particles to the compactor, the controller also provides inputs to vacuum apparatus 111, which draws a vacuum on each successive compartment of valve 74, and pressure source 113, which subsequently pressurizes the evacuated compartment.

By employing automatically controlled valves, as described above, relatively small selected amounts of biological waste may be continuously added to the operating sterilization chamber. Waste does not have to be introduced in discrete mass or bulk quantities. A large steam chamber is not required and energy efficiency is improved considerably.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. An apparatus for sterilizing biological waste material comprising:
   a shredder mechanism;
   means for introducing waste material into said shredder mechanism, which shredder mechanism chops the waste material into particles of reduced size;
   a preheating chamber;

first transmittal means communicably interconnected between said shredder mechanism and said preheating chamber;

controller means for directing said first transmittal means to selectively transmit particles from said shredder mechanism to said preheating chamber;

means responsive to said controller means, for introducing free-flowing steam of at least 140 degrees Fahrenheit into said preheating chamber to directly contact and preheat said particles;

a sterilization chamber;

a valve assembly interconnected between said preheating chamber and said sterilization chamber and being selectively opened by said controller means to transmit a selected amount of said preheated particles from said preheating chamber to said sterilization chamber; and means, responsive to said controller means, for introducing into said sterilization chamber hotter free-flowing steam having a temperature that is greater than the temperature of steam that is introduced into said preheating chamber and of at least 248° Fahrenheit to directly contact and heat said preheated particles such that said particles are sterilized.

2. The system of claim 1 in which said first transmittal means include a storage chamber disposed between said shredder mechanism and said preheating chamber, a first valve interconnecting said shredder mechanism and said storage chamber, said first valve being selectively opened to transmit chopped particles from said shredder mechanism to said storage chamber, a second valve interconnecting said storage and preheating chambers, said second valve being selectively opened to transmit chopped particles from said storage chamber to said preheating chamber.

3. The system of claim 1 in which a jacket is formed about said preheating chamber and means are provided for introducing steam into said jacket to heat the exterior surface of said preheating chamber.

4. The system of claim 1 in which a jacket is formed about said sterilization chamber and means are provided for introducing steam into said jacket to heat the exterior surface of said sterilization chamber.

5. The apparatus of claim 1 in which said first transmittal means and said valve assembly include respective star valves.

6. The apparatus of claim 1 further including means, responsive to said controller means, for drawing a vacuum on said selected amount of preheated particles before said particles are introduced to said sterilizing chamber.

7. The system of claim 1 in which said means for introducing include a feed hopper connected to said shredder mechanism.

8. The system of claim 7 further comprising purge means that include means for introducing steam into said feed hopper to kill bacteria in said feed hopper.

9. The system of claim 1 further including a preheating conveyer for conveying said particles through said preheating chamber from said first transmittal means to said second transmittal means.

10. The system of claim 9 in which said preheating conveyer includes means for dispersing said particles as said particles are conveyed through said preheating chamber.

11. The system of claim 1 further including a sterilization conveyer for conveying said preheated particles through the sterilization chamber from said second transmittal means to said third transmittal means.

12. The system of claim 11 in which said sterilization conveyer includes means for dispersing said particles as said particles are conveyed through said sterilization chamber.

13. The system of claim 1 further including a particle compactor and third transmittal means communicably interconnected with said sterilization chamber and said compactor for transmitting said sterilized particles to said compactor wherein said particles are compacted.

14. The system of claim 13 in which said third transmittal means include a valve apparatus, interconnecting said sterilization chamber and said compactor said valve apparatus being selectively opened to transmit said sterilized particles from said sterilization chamber to said compactor.

15. The apparatus of claim 14 in which said valve apparatus includes a star valve.

16. An apparatus for sterilizing biological waste material comprising:

a shredder mechanism;

means for introducing waste material into said shredder mechanism, which shredder mechanism chops the waste material into particles of reduced size;

a preheating chamber;

means for sensing the temperature within said preheating chamber;

first transmittal means interconnected between said shredder mechanism and said preheating chamber and comprising a storage chamber, a first valve interconnected between said shredder mechanism and said storage chamber and a second valve interconnected between said storage chamber and said preheating chamber;

controller means, responsive to operation of said shredder mechanism, for opening said first valve to transmit chopped particles from said shredder mechanism to said storage chamber, and responsive to a temperature in said preheating chamber at least 165° F. and no greater than 210° F. for a selected time, for opening said second valve to transmit particles from said storage chamber to said preheating chamber;

means, responsive to said controller, for introducing free flowing steam of at least 140° into said preheating chamber to directly contact and preheat said particles;

a sterilization chamber;

means for sensing the temperature within said sterilization chamber;

a valve assembly interconnected between said preheating chamber and said sterilization chamber and being selectively opened by said controller means for a selected time when the temperature in said sterilization chamber is at least 248° F. to transmit a selected amount of said preheated particle from said preheating chamber to said sterilization chamber; and means, responsive to said controller means, for introducing into said sterilization chamber hotter free-flowing steam having a temperature that is greater than the temperature of steam that is introduced into said preheating chamber and of at least 248° Fahrenheit to directly contact and heat said preheated particles such that said particles are sterilized.

17. The apparatus of claim 16 further including means, responsive to said controller means, for drawing a vacuum on said selected amount of preheated particles before said particles are introduced to said sterilizing chamber.

* * * * *